United States Patent [19]

Poler

[11] 4,249,271
[45] Feb. 10, 1981

[54] INTRAOCULAR LENS

[76] Inventor: Stanley Poler, 78 E. Second St., New York, N.Y. 10003

[21] Appl. No.: 57,323

[22] Filed: Jul. 13, 1979

Related U.S. Application Data

[63] Continuation-in-part of Ser. No. 9,926, Feb. 6, 1979, abandoned.

[51] Int. Cl.³ .......................... A61F 1/16; A61F 1/24
[52] U.S. Cl. ..................................................... 3/13
[58] Field of Search ......................................... 3/13, 1

[56] References Cited

U.S. PATENT DOCUMENTS

| | | | |
|---|---|---|---|
| 3,925,825 | 12/1975 | Richards et al. | 3/13 |
| 3,975,779 | 8/1976 | Richards et al. | 3/13 |
| 4,110,848 | 9/1978 | Jensen | 3/13 |
| 4,159,546 | 7/1979 | Shearing | 3/13 |
| 4,174,543 | 11/1979 | Kelman | 3/13 |

Primary Examiner—Ronald L. Frinks
Attorney, Agent, or Firm—Hopgood, Calimafde, Kalil, Blaustein & Lieberman

[57] ABSTRACT

The invention contemplates improved intraocular-lens structures for use as implants in ophthalmological surgery, the lens being a replacement for a cataract-clouded natural lens, and the replacement being installed in the pupil at the iris as the operative step following removal of the cataracted lens. The lens features adapter structure assembled to an optically finished lens element and including plural angularly spaced stabilizing feet which are formed integrally with the body of the adapter and which are axially offset from the adapter body to permit the stabilizing feet and the adapter body to engage opposite sides of the iris.

39 Claims, 20 Drawing Figures

INTRAOCULAR LENS

RELATED CASE

This application is a continuation-in-part of my copending application, Ser. No. 9,926, filed Feb. 6, 1979 and now abandoned.

BACKGROUND OF THE INVENTION

This invention relates to structures for making an improved lens implant, as a replacement for a cataract-clouded or otherwise diseased natural lens. The invention represents improvement over structures described in my U.S. Pat. No. 4,122,556 and over my various other patent disclosures referred to in said patent. Reference is therefore made to said patent and disclosures for greater background detail as to structure, and manufacturing and manipulating technique.

Regardless of the structure of an intraocular lens and its mount, relatively great skill is required for installation at or through an iris opening, if post-operative trauma are to be avoided. The likelihood of such trauma is also reduced, to the extent that lens mounting structure imposes least restriction upon normal aperture responses of the iris.

BRIEF STATEMENT OF THE INVENTION

It is an object of the invention to provide improved mounting structure for an intraocular lens.

Another object is to provide such structure lending itself to simplified installation at or via the iris.

It is a specific object to provide such structure with iris-stabilizing means placing substantially reduced restriction upon the iris, as compared with prior constructions.

It is another specific object to provide such structure with stabilizing means adapted to provide lens-positioning support within and from the inner wall of the crystalline-lens sac, following invasive surgery to remove cataracted material from the sac.

It is also a specific object to provide such structure which lends itself to posterior implantation in a human eye and which is inherently resistive against such secondary membrane growth (i.e., corpuscular regrowth) as might otherwise obscure or degrade optical performance of the implanted lens.

Still another specific object is to achieve the above objects with structure which is inherently capable of securely and accurately positioning an optically finished glass lens element.

A further specific object of the invention is to provide two-piece lens-adapter structure which is modular to the extent that it is inherently adaptable with little or no modification to one or more different modes of support within the eye, such modes being selectable at the surgeon's option, viz.: iris-supported, lens-capsule suspended, posterior-chamber or anterior-chamber supported.

The foregoing and other objects and features of the invention are achieved in an illustrative series of embodiments by providing annular adapter structure which axially retains itself against both axial sides of the peripheral rim of the lens element to which it is assembled. And plural stabilizing feet are provided as radially outward projections which have axially offset integral connection to the radially inner edge of the annular body of the adapter. In several of the forms to be described, the adapter body and its stabilizing feet are formed from compliant sheet material, the axial-offset and radially-projecting parts of the stabilizing feet being permanently bent to ultimate configuration, in a secondary operation. The ability to use the same adapter blank for production of lens-mounting structure wherein the axial offset of stabilizing feet can be at selected different radii about the axis of optical symmetry is significant, in that the structure of the invention can be simply completed to such radius of stabilizing foot-offset as a particular ophthalmological surgeon may prescribe for a particular patient, such radius being selectable, for example, within a 2:1 range of prescribable radii, for the case of an implanted optically finished glass lens of 5 mm diameter.

DESCRIPTION OF PREFERRED EMBODIMENTS

Preferred embodiments of the invention are shown in accompanying drawings, taken in conjunction with ensuing text. In said drawings.

Figure 1:
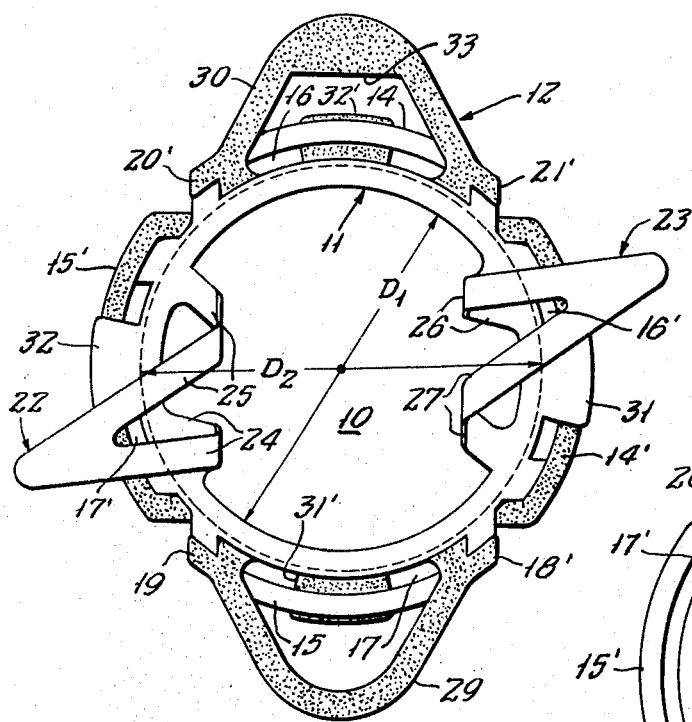
FIG. 1 is a view in elevation of an intraocular lens of the invention, complete with assembled mounting structure, as viewed from the posterior side.
Figure 3:
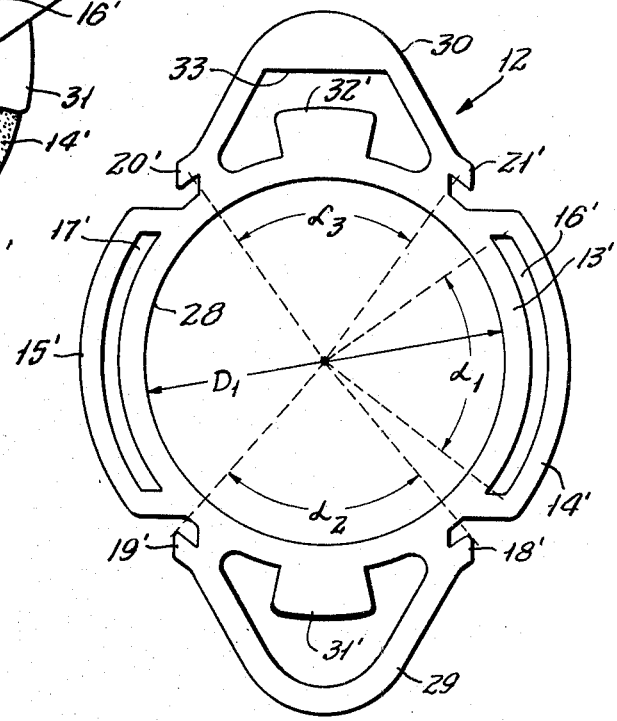
FIGS. 2 and 3 are blank outlines of the respective mounting parts employed in the structure of FIG. 1.
Figure 2:
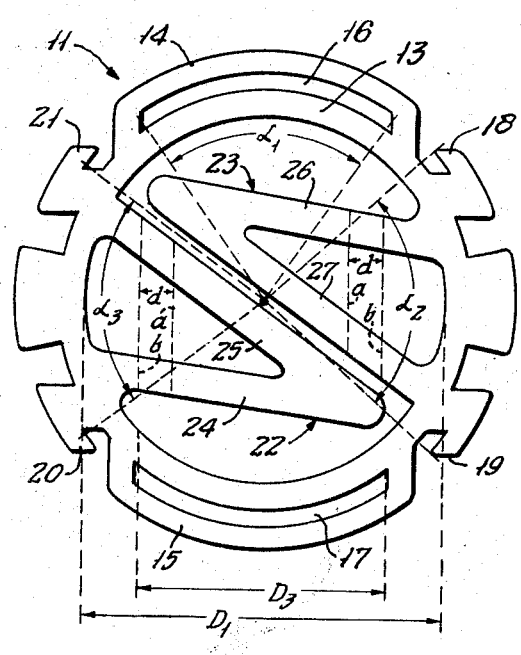

In FIGS. 1 to 3, the invention is shown in application to mounting structure for a finished optical lens element 10 to be surgically implanted in a human eye, relying upon the iris for stabilized support of the implant. The mounting structure comprises two parts 11 (FIG. 2) and 12 (FIG. 3) which circumferentially continuously overlap opposite axial sides of the rim or peripheral region of lens 10 and which are connected to each other at angularly spaced locations adjacent the lens periphery. Each of these parts, such as the posterior part 11, is characterized by a circumferentially continuous body portion 13 having a circular inner edge of diameter $D_1$ less than the diameter $D_2$ of lens 10 and otherwise in full radial overlap with the lens periphery; because of similarity of certain features of both the posterior part 11 and the anterior part 12, the same identifying numbers as used in FIG. 2 are adopted for corresponding features of FIG.

3, with primed notation. Thus, with the parts 11-12 assembled to each other and to lens element 10 in FIG. 1, the body portion 13 of the posterior part 11 circumferentially continuously laps the posterior side of the peripheral region of the lens element, and the body portion 13' of anterior part 12 similarly laps the corresponding anterior region of the lens element.

For connected assembly of parts 11-12 to each other, the peripheral regions of both body portions 13-13' similarly formed with hook and slot formations having diametrically opposite symmetry in diametrically opposite quadrants about the central optical axis. Thus, within a first pair of diametrically opposed quadrants, first and second diametrically symmetrical extensive arcuate tab projections 14-15 are formed with arcuate slots 16-17, of substantial angular extent $\alpha_1$ approaching but less than 90 degrees. And within the remaining or second pair of diametrically opposed quadrants, first and second pairs of diametrically symmetrical hook formations 18-19 and 20-21 project in the circumferentially outward direction with respect to the involved quadrant. The hook formations of posterior member 11 are designed for interlocked engagement in the arcuate-slot formations 16'-17' of anterior member 12, while the hook formations 18'-19' and 20'-21' of anterior member 12 have interlocked engagement in the arcuate-slot formations 16-17 of posterior member 11. To this end, the hook ends in a given quadrant are at an angular spread $\alpha_2$ which exceeds the effective slot width $\alpha_1$, and the closed end of the hook openings in a given quadrant are at an angular spread $\alpha_3$ which is less than the effective slot width $\alpha_1$.

In accordance with a feature of the invention, the inner circular region of the posterior part 11 has integrally formed structure which, after permanent bending in a secondary operation, defines angularly spaced feet (or haptics) 22-23 for ultimate stabilizing engagement with the posterior side of the iris. Each of the feet 22 (23) is an open triangle comprising spaced legs 24-25 (26-27) integrally connected at their ends to angularly spaced locations along the inner circular edge of the body portion 13, and integrally connected to each other at their outer ends, the connections to body 13 being within the opposed quadrants characterized by hook formations 18-19 and 20-21. Inner and outer parallel right-angle fold alignments a-b establish at a a regional diameter, slightly exceeding the separation $D_3$ between the inner fold alignments a, at which diameter the short span d between adjacent folds a-b will define the axial offset (through the iris opening) by which feet 22-23 become engageable with the posterior of the iris. Generally speaking, the offset between adjacent folds a-b (and therefore the axial offset between feet 22-23 and the body 13) is about half a millimeter, and the regional diameter of iris transit by the offsetting spans of feet 22-23 is a matter for professional prescription, as in the 2:1 range of 2 to 4 mm for the dimension $D_3$. It will be understood that prescription for the dimension $D_3$ determines the fold alignments a and that the fold alignments b will be at offset d therefrom and thus also prescription-dependent.

In FIG. 3, it is seen that the anterior mounting part 12 has body and interlocking-connection features as described for the posterior part 11. However, part 12 differs in that its central opening has a circumferentially continuous inner edge 28, and arched radially outward stabilizing foot formations 20 (30) integrally connect the hook formations 18'-19' (20'-21') of the associated quadrant. Generally speaking, the overall span between tips of feet 29-30 and between tips of the formed posterior feet 22-23 is at least no greater than substantially 10 mm, being preferably in the range of 6 to 9 mm.

The fully assembled structure is seen in FIG. 1 to involve eight angularly spaced hook-to-slot interlocking engagements around the rim of lens element 10, with the feet 29-30 projecting on one diametrical alignment of symmetry for stabilizing anterior engagement with the iris, and with feet 22-23 projecting on a second generally diametrical alignment for angularly interlaced posterior engagement with the iris. The hook and slot patterns of the respective parts 11-12 are 90-degrees offset with respect to each other, to enable the described interlocking relation. And the lens element 10 is positively retained by and between circumferentially continuous body surfaces 13-13', with concentric mounting assured by the eight interlocking engagements. Finally, short radially outward integral tab formations 31-32 (31'-32'), between adjacent hook formations 18-19 and 20-21, radially overlap central regions of slotted projections 14'-15' (14-15) to provide additional mutuality of body-member support, and a straight-chord inner edge 33 of foot formation 30 enables keyed engagement with a suitably characterized manipulating tool or instrument, as described in detail in my above-identified patent.

Figure 1A:
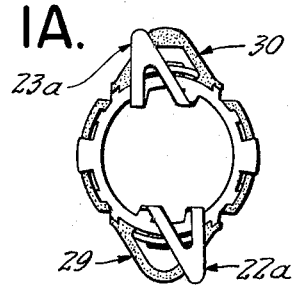
FIG. 1A is a view similar to FIG. 1 and on a reduced scale, to show a modification.
Figure 2A:
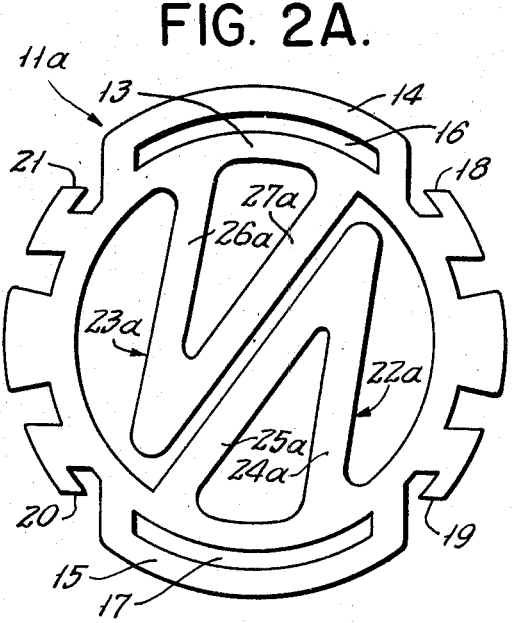
FIG. 2A is a view similar to FIG. 2 to show the modified part, substituted for the FIG. 2 part, to make the assembly of FIG. 1A.

The stabilizing-foot pattern of the embodiment of FIG. 1 may be briefly described and identified as a four-loop cross, in that the opposed feet 22-23 of the body member 11 are assembled in angular interlace with the opposed feet 29-30 of the other body member 12. Necessarily therefore, any axial force attributable to foot engagement with the iris will be distributed in the posterior direction, in angular interlace with such force, in the opposite or anterior direction. Some surgeons prefer not to implant a lens which has the potential for such interlacing of oppositely directed local force upon the iris, and to meet the preference of such surgeons, I illustrate in FIG. 1A, a lens with a two-piece mount which may exactly meet the description given for FIG. 1, except that the body member 11a of FIG. 2A is substituted for the body member 11 of FIG. 2, body member 11a being assembled to body member 12 (FIG. 3). All hook and slot formations of FIG. 2A may be exactly as described for FIG. 2 and have therefore been given the same reference numbers, but the integral formation of connected pairs of spaced legs (24-25 and 26-27, in FIG. 2) has been angularly repositioned 90 degrees; these legs are therefore given the different but corresponding numbers 24a-25a (at foot 22a) and 26a-27a (at foot 23a). The result, upon permanently setting the fold alignments of legs 24a-25a (26a-27a), is to create the holding structure of FIG. 1A, wherein the feet 22a–29 are in axially spaced but angular register to define a first iris clip, while the corresponding but diametrically opposite feet 23a–30 similarly define a second iris clip.

Figure 4:
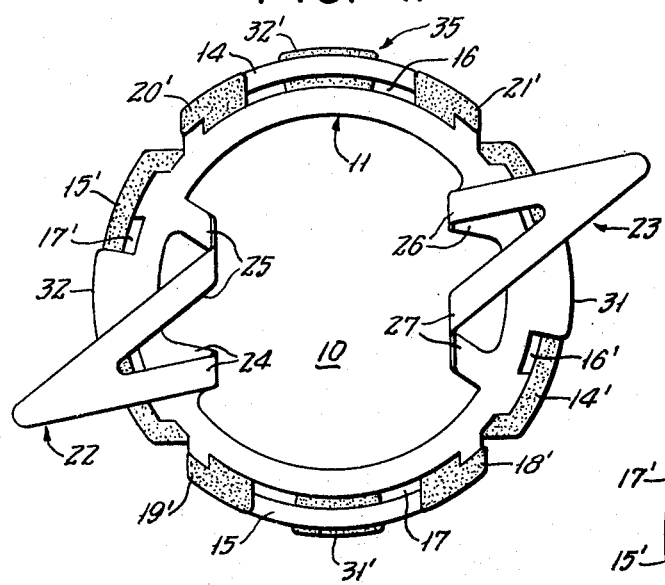
FIG. 4 is a view similar to FIG. 1 to show another embodiment.
Figure 5:
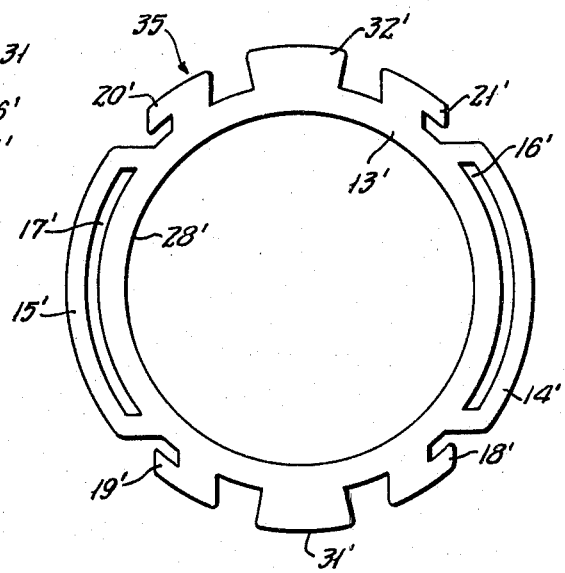
FIG. 5 is a view similar to FIG. 3 to show the mounting part which replaces that of FIG. 3 to make the embodiment of FIG. 4.

The embodiment of FIG. 4 makes use of mounting structure involving the posterior member 11 of FIG. 2 and the anterior member 35 of FIG. 5. The member 35 may in all respects be as described for member 12 of FIG. 3, except for elimination of the feet 29-30 for anterior engagement with the iris. The corresponding parts of FIGS. 4 and 5 therefore have the same reference numbers as in FIGS. 1 to 3.

All discussion thus far has presumed the surgeon's election to utilize the iris for implant stabilizing and to completely remove the cataracted lens. Some surgeons, on the other hand, may elect to remove merely the cataracted front surface of the lens and the nucleus of the lens, thus leaving a major part of the lens capsule (i.e., the sac) as a base for implant mounting. The structural arrangement of FIG. 4 serves the surgeon who elects to rely upon the growth of capsule tissue adjacent the implanted body mount, to retain the implant. For example, according to one operational procedure, at the time of implantation, the feet 22-23 are the only parts of the FIG. 4 assembly to pass through the iris opening, and they are compliantly inwardly deflected to permit insertion into the excavated lens capsule or sac, whereupon they are released, for gentle resiliently (radially outward and axially inwardly) loaded stabilizing contact with the inner wall surface of the sac, it being noted that during insertion the iris is treated to assure against dilation, so that lens 10 and the rings of circumferentially engaged body members 11-35 will axially locate against the anterior of the iris. The surgery is completed and the patient is kept at rest, face up, and locally treated (as for a period of days) with suitable drug medication to assure against iris dilation, while a tissue attachment is allowed to develop between the peripheral inner wall surface of the capsule (sac) and the flexibly compliant posterior feet 22-23. For this period of days, the implanted lens 10 and most of the haptic are anterior and adjacent to the iris. The operation is completed, once there has been a sufficient tissue attachment to feet 22-23, by applying medication to cause transient iris dilation, whereupon the lens and its mount are released for automatic axial withdrawal through the iris opening and to a position of rest that is posterior to the iris and in outer circumferential adjacency to regrowth tissue of the capsule. In the course of time, such tissue attaches to the circumferentially continuous body confines established by and between members 11—35 and the periphery of lens 10; and the use of glass at lens 10 is found to substantially inhibit tissue regrowth, so that such regrowth at the implant is essentially limited to the circumferential region of the mount, with the lens 10 remaining clear and substantially free of regrowth tissue.

Figure 6:
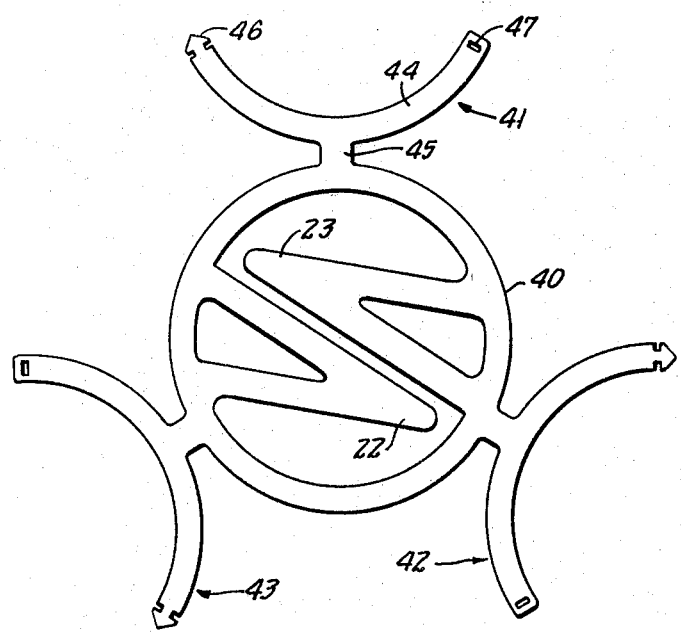
FIG. 6 is a blank outline for another embodiment of mounting structure of the invention.
Figure 7:
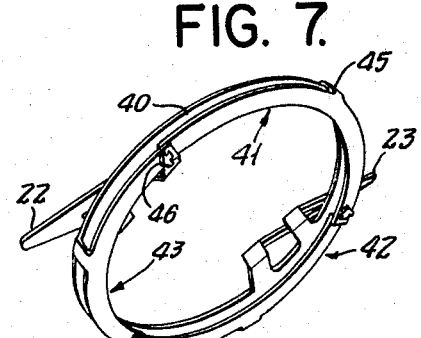
FIG. 7 is a perspective view of the embodiment of FIG. 6, in its ultimately formed configuration.

The embodiment of FIGS. 6 and 7 illustrates application of the invention to a single piece lens-retaining mount, i.e., formed from a single piece of thin compliant sheet having the blanked initial outline shown in FIG. 6. Again, the body structure 40 is seen to be a flat circumferentially continuous annulus, with the integral inward foot formations 22-23 which have already been described. To retain as assembled lens element, the body 40 has n like angularly spaced outward lug formations 41-42-43 integrally formed therewith. Each of these lug formations is shown to comprise an arcuate segment 44, having a short bridging connection 45 to body 40, the arcuate curvature at 44 being equal and initially opposite to the adjacent region of body 40. And the arcuate extent of each segment 44 slightly exceeds $2\pi/n$ radians about the center of body 40. This being the case, and upon 180-degree folding of lugs 41-42-43 at their bridge connections 45 (i.e., locally around the periphery of a lens element positioned for axial rim abutment with body 40), the segments 44 may be end-lapped to define connected retaining body structure for the other axial side of the lens element. As shown, hook-and-slot engagement 46-47 of such lapped ends serves to retain circumferential continuity of such retention.

Figure 8:
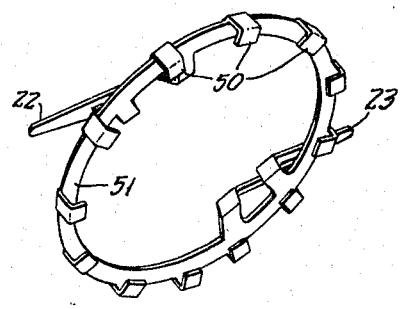
FIG. 8 is a similar perspective view to illustrate another embodiment.

The arrangement of FIG. 8 exemplifies further single-piece retainer structure wherein plural angularly spaced retainer lugs 50 are initially radially outward projections from the circumferentially continuous thin flat body 51 but are permanently deformed locally around spaced locations of the lens-element rim, with subsequent permanent radially inward deformation for retaining engagement with the other axial side of the lens-element rim. Again, the axially inwardly offset feet 22-23 will be recognized, bent as described from their initially flat integral connection to the inner edge of the central circular opening of body 51.

Figure 9:
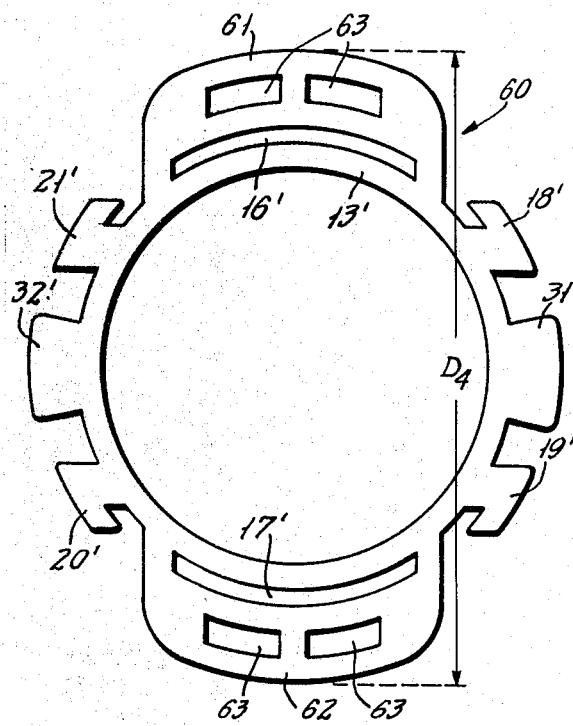
FIG. 9 is a blank outline of one part of a further embodiment.
Figure 9A:
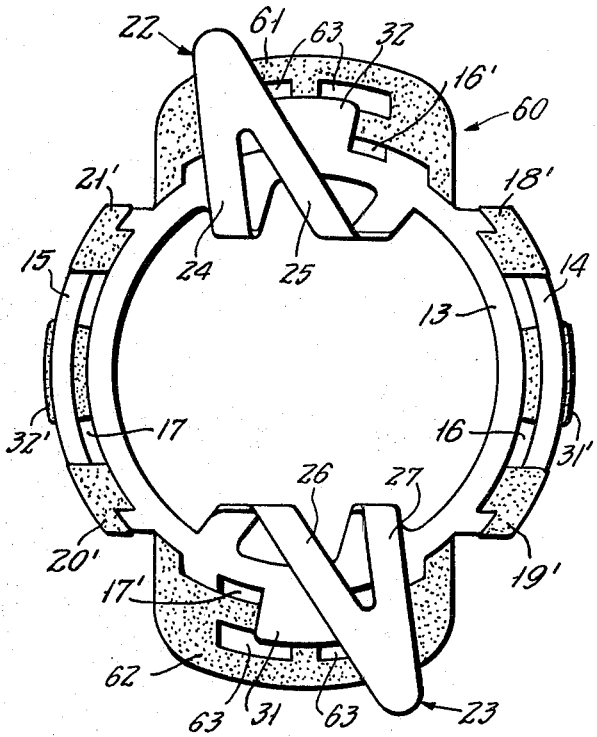
FIG. 9A is a view in elevation of a lens and mount incorporating the part of FIG. 9.

The body member 60 of FIG. 9 represents a modification of body member 35 (FIG. 5), wherein diametrically opposed relatively short radial flange elements 61-62 span the respective slotted regions 16'-17'. The relatively short radial extent is apparent from an overall diametrical dimension $D_4$ (such as about 7 mm) which is sufficient to safely locate axially against the anterior of the iris, without contacting any outer-wall part of the anterior acqueous chamber of the eye. The body member 60 is assembled with a lens 10 and a body member 11 (FIG. 2) to produce the assembly of FIG. 9A, wherein the feet 22-23 will be understood to be for operative insertion through the iris, to stabilize against the inner surface of the excavated natural lens capsule (sac), as in the manner described above for two-stage implantation of the assembly of FIG. 4. The form of FIGS. 9 and 9A provides the added assurance, via openings 63 in flange elements 61-62, that, after iris dilation to allow the lens and its mount to pass completely to the posterior chamber, tissue regrowth may establish more positive attachment for lens-support purposes, as will be understood.

The body member 65 of FIG. 10 is again similar to that of FIG. 5, except that local apertures at spaced loops 66-67, formed integrally with the arcuate tab 14', provide greater manipulating access for suture connection to the anterior of the iris. Assembly to lens 10 and a second body member 11 (FIG. 2) will again afford stabilizing contact of feet 22-23 with the posterior of the iris, and centering contact is via the spans d between folds a-b of feet 22-23.

Figure 10:
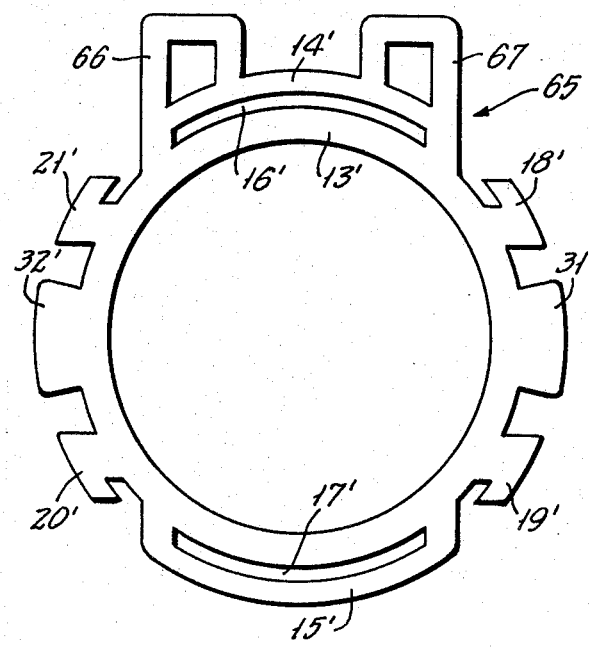
FIGS. 10 through 16 are blank outlines of successive further embodiments.
Figure 11:
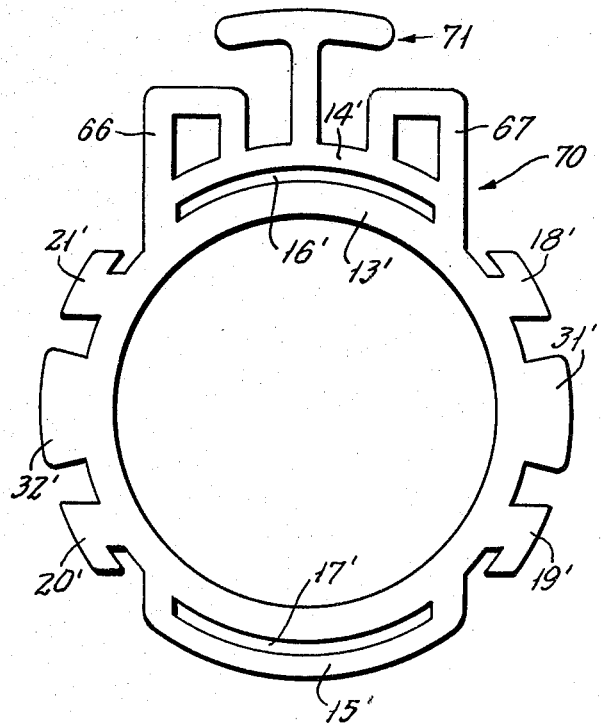

The body member 70 of FIG. 11 will be recognized as only a small departure from that of FIG. 10, in that a T-shaped formation 71 projects radially from the arcuate tab 14' between loops 66-67. Again, a lens 10 will be understood to be retained and supported by and between member 70 and a member 11 (FIG. 2) assembled thereto. The T-formation 71, being integrally formed with member 70, will be seen to accommodate the surgeon who would opt for a local incision in the base of the iris, with manipulated insertion of the laterally spread outer arms of T-formation 71 through the incision, thereby providing an iris-anchored anterior suspension, with posterior foot stabilization as previously described.

Figure 12:
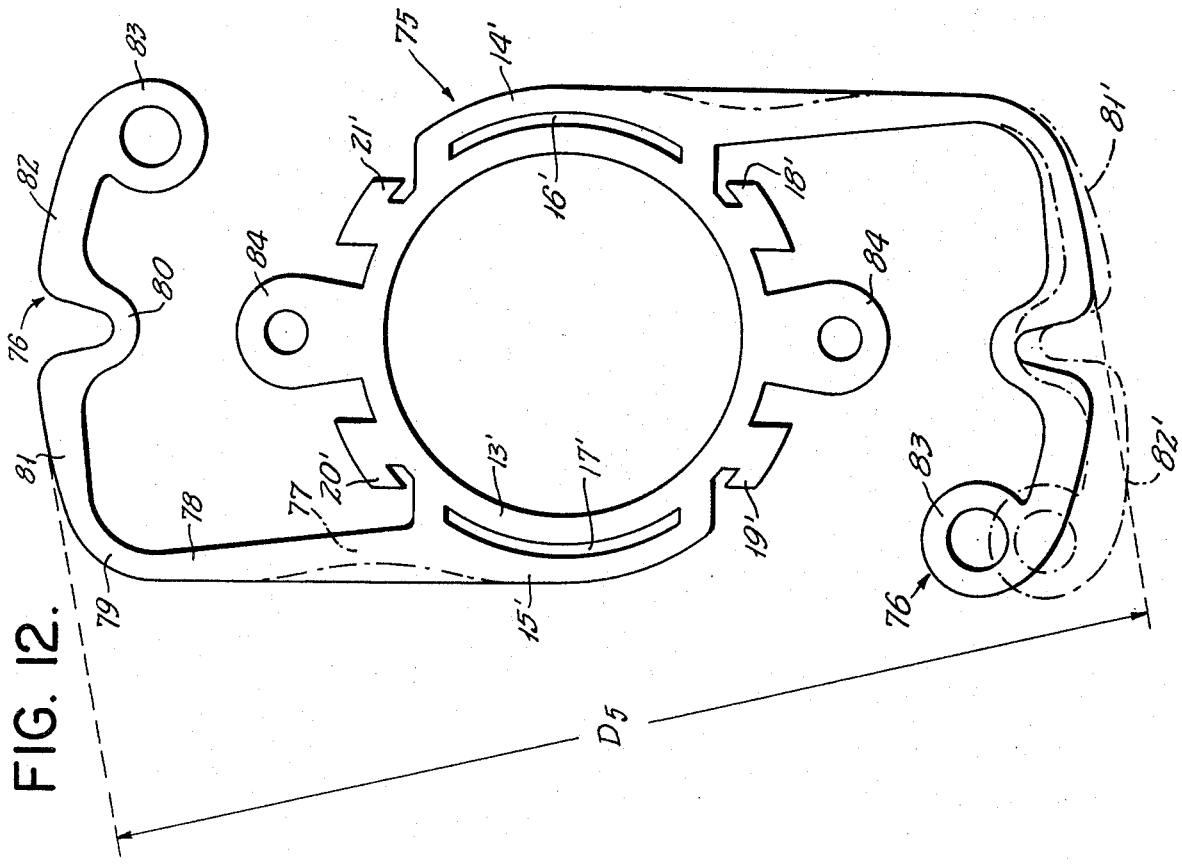

The body member 75 of FIG. 12 is designed with hook and slot formations as in FIG. 3, but with angularly spaced stabilizing radially outward foot formations 76 which are wholly radially compliant in their positioning engagement with eye chamber structure, in front of or behind the iris, as the surgeon may select. The lens 10 is retained by hook-and-slot engagement of a plain locking-ring body member 35 (FIG. 5) to the cooperating slot-and-hook formations of member 75. As shown, the radially compliant action results from gradual taper (with attendant moment-of-inertia reduction) along a primary arm element 78 formed with the ring body 13' at 14' (15'), and from localized moment-of-inertia reduction at 79 and at 80 between intermediate and outer limbs 81-82 of each of the fully cantilevered formations 76; a further localized section reduction in arm 78 is suggested by phantom line 77, for greater radial compliance. It will be understood that the solid-line outlines of FIG. 12 delineate the limb formations 81-82 in their compliantly articulated relationship after deformation to conform to chamber-wall contact at the base of the iris, the shape prior to deformation being more as suggested by phantom outlines at 81'-82' for one of the formations 76.

For the circumstance that body member 75 is to be used for a posterior aqueous chamber implantation, the ends of limbs 82 are apertured at loop formations 83, and the tabs between adjacent hook formations 18'-19' and 20'-21' are similarly apertured at loop formations 84. It will be understood that by using a suture filament between one loop 83 and the more distant loop 84, both these loops can be temporarily drawn together to completely retract one of the feet 76, and that a similar temporary connection between the remaining loops 83-84 will enable corresponding retraction of the other foot 76, thereby permitting easier manipulation of the complete assembly through the iris opening. Once correctly oriented in the posterior chamber, the filaments can be released and withdrawn to permit feet 76 to assume their intended roles.

Figure 13:
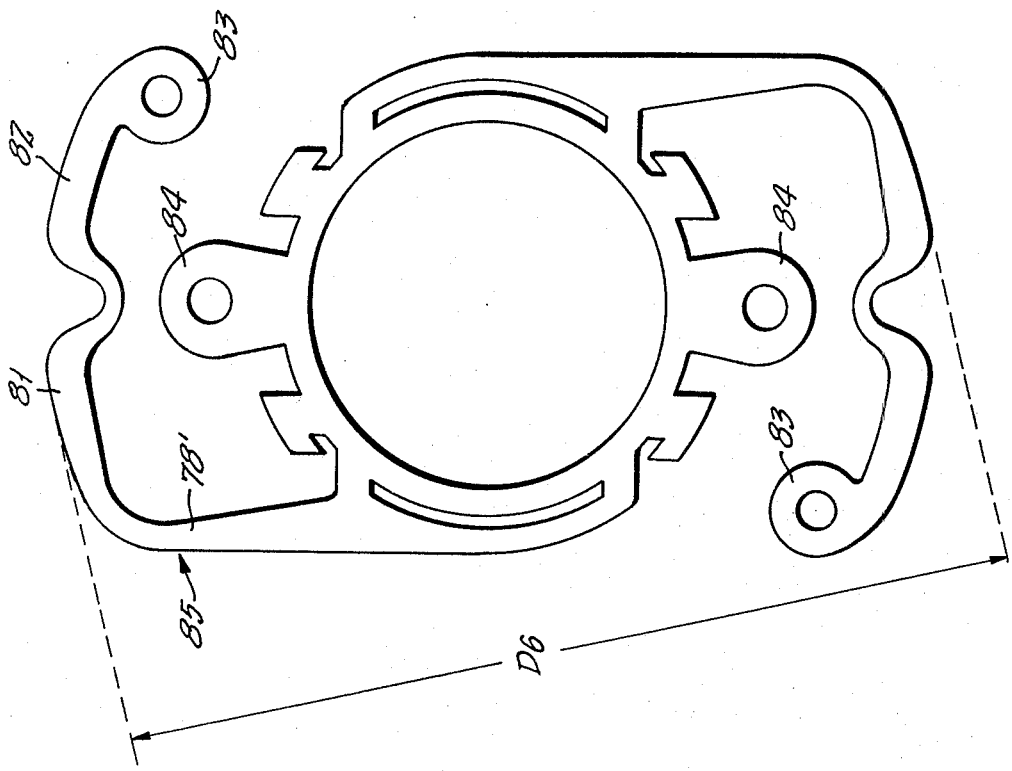

The body member configuration 82 of FIG. 13 may be in all respects as described for the part 75 of FIG. 12, except for the radially shorter primary-arm element 78' of FIG. 13; the same reference numerals are therefore used for the remainder of FIG. 13. Assembly to lens 10 and body member 35 (FIG. 5) is as previously described. The indicated shorter-arm proportion accounts for an overall installed diameter $D_6$ in FIG. 13 which is smaller than the corresponding overall installed diameter $D_5$ which is shown for the member 75 in FIG. 12. It will be understood that the smaller dimension $D_6$ of member 85 in FIG. 13 will typically be 10.5 to 11.5 mm, for radially outward release and compliant stabilizing contact within an excavated lens capsule or sac.

Figure 14:
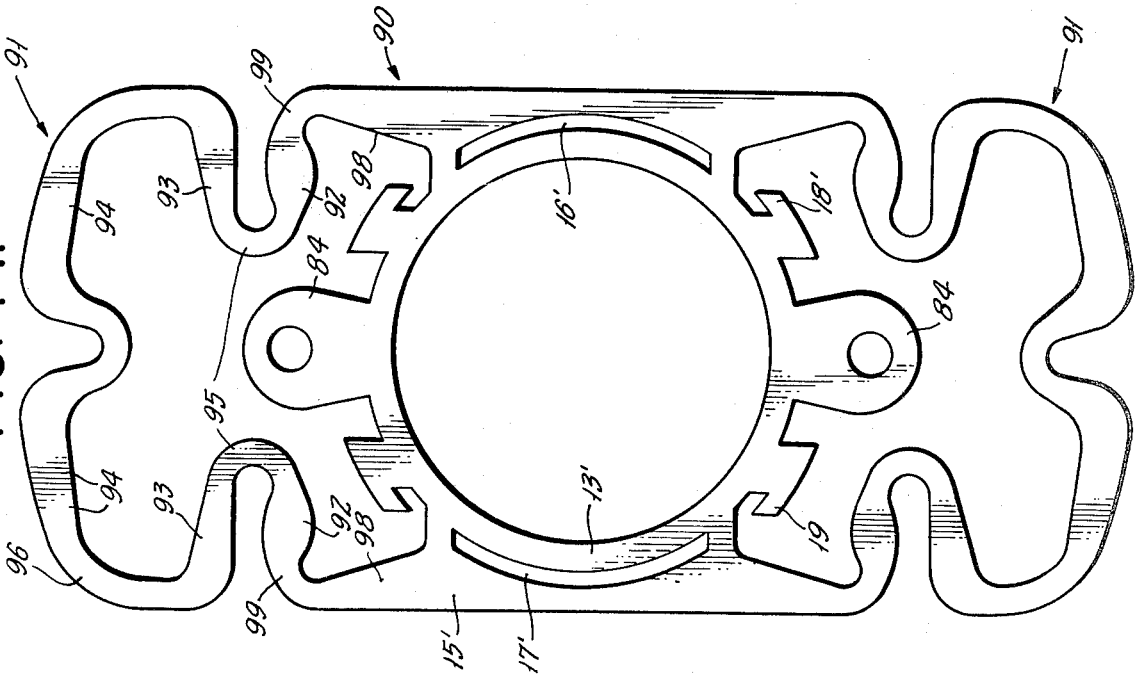

The body member 90 of FIG. 14 represents modification of the configurations of FIGS. 12 and 13, to the extent of providing more uniform distribution of radially compliant suspension of the lens 10 to which it is assembled, using the locking ring member 35 of FIG. 5. In FIG. 14, each of the diametrically opposite suspension-foot formations 91 is a loop of interconnected limbs 92-93-94, having integral compliant connection to each other at 95-96-97 and to a body-pedestal formation 98, at 99. It will be appreciated that a lens 10, mounted as indicated via a body member 90, may be radially suspended by reference to the anterior-chamber confines or by reference to the posterior-chamber confines, releasable filamentary connection of each foot 91 to its opposite loop formation 84 being an acceptable technique of transient size reduction for trans-iris transport and manipulation.

Figure 15:
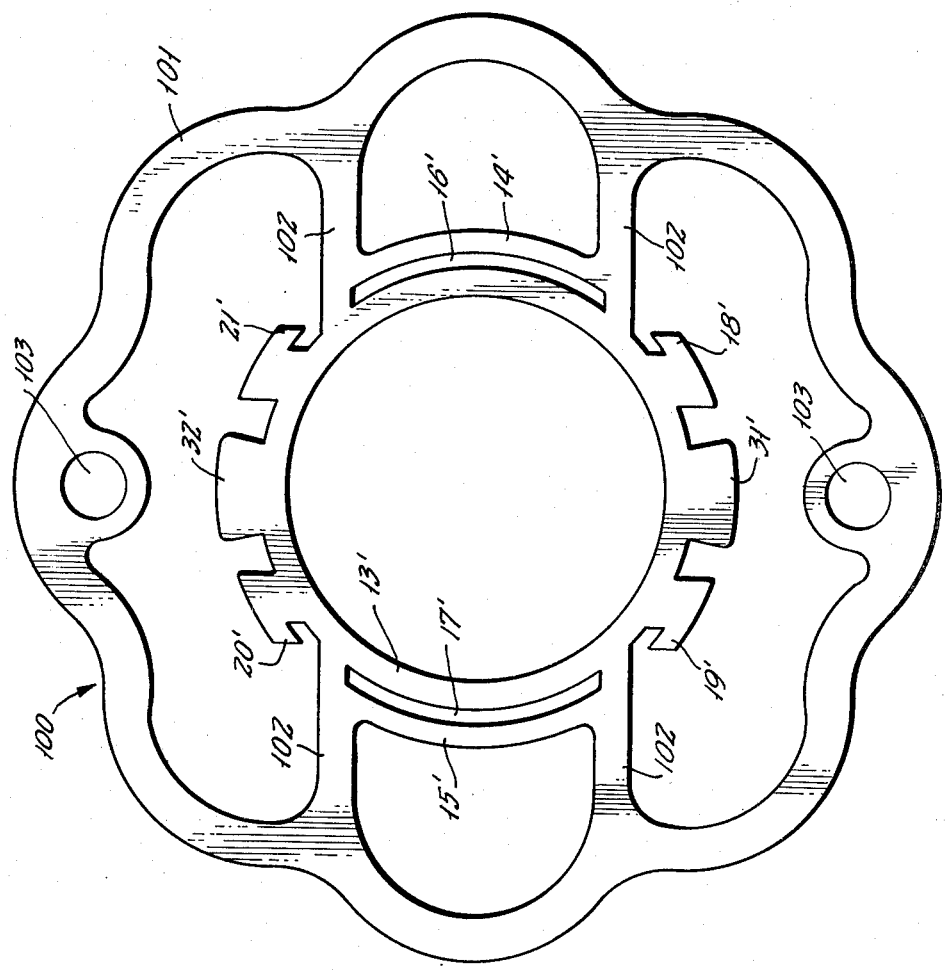

FIG. 15 represents a still further body-member modification, particularly suited to lens-capsule (sac) installation when assembled to a plain locking ring 35 (FIG. 5) and with an interposed lens 10. The construction of the body member 100 of FIG. 15 features a continuous outer ring 101 characterized by gentle radial undulations and connected by opposed pairs of radial struts 102 to the body 13', across the angular limits of the respective slotted regions 16'-17'. A central aperture 103 at the center of each of the larger radially compliant spans of ring 101, e.g., bridging hook formations 20'-21', enables transient use of a filament of draw these spans together and thus facilitate trans-iris manipulation, for subsequent orientation, release and stabilization, referenced to the confines of an excavated lens capsule (sac).

Figure 16:
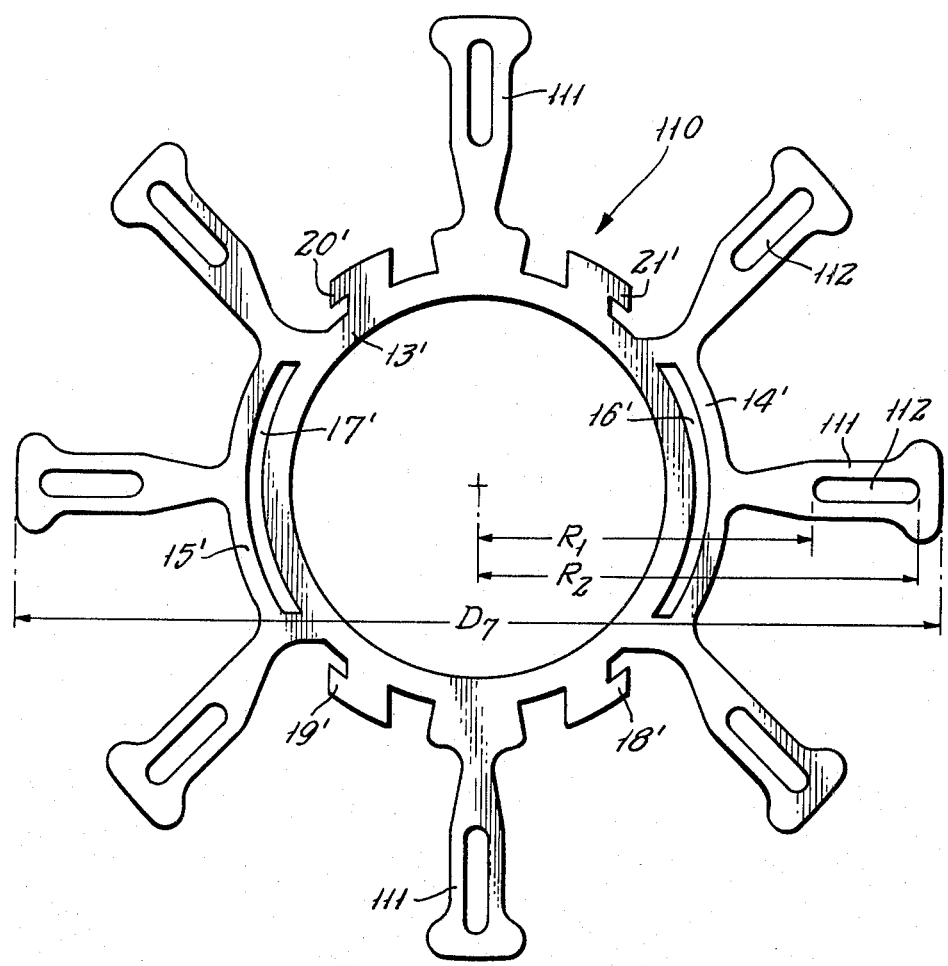
Figure 17:
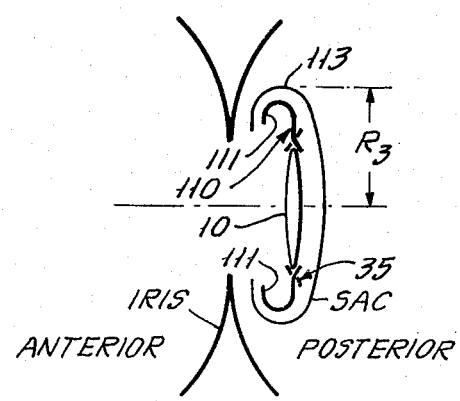
FIG. 17 is a simplified and somewhat schematic sectional view to show installed implantation of a lens and mount incorporating the part of FIG. 16.

The body-member arrangement 110 of FIG. 16 is a further illustration of a radially compliant means of implanted-lens suspension. Its basic hook-and-slot formations will be recognized, and it is designed for assembled retention of a lens 10 using a plane locking ring 35 (FIG. 5) in the manner already described. Plural radial foot projections 111 extend from angularly spaced locations on the basic body ring of member 110, to an overall diametral extent $D_7$, say 11.5 to 12.5 mm, which exceeds the maximum available mounting diameter within an excavated lens capsule or sac. A slotted region 112 in each of the foot projections 111 renders them more bendable and hence more capable of gentle readially compliant suspension of the mounted lens, the radial extent $R_1-R_2$ between inner and outer slot limits being selected to be primarily within (i.e., less than) but nevertheless preferably to include the available mounting radius $R_3$ (about 5.5 mm) within the excavated sac 113 (see FIG. 17). Operatively, a lens 10 mounted by assembled body members 110-35 is transported through the iris opening, using a single releasable filament through all slots, for transient overall size reduction, and using a manipulative tool having releasable engagement with the lens rim. Once past the iris, and suitably oriented, the filament is withdrawn, thereby releasing all feet to restore their FIG. 16 appearance, the feet 111 being then in a radial plane between the iris and the excavated sac 113. The assembly is then further inserted into the sac 113 until feet 111 become deflected and retained by sac-wall engagement, as schematically shown in FIG. 17. The lens 10 is then in a position which as faithfully as possible duplicates the position of the original natural lens, prior to its development of the cataract condition which dictated its removal. It follows that the patient will achieve maximum reinstatement of his original vision capabilities, including a wide angle of peripheral perception.

The described body-member configurations and assemblies will be seen to utilize basic two-part lens-mounting structure which is to an extent modular, in that a wide variety of different anterior and posterior suspensions can be provided, to suit the professional preference or decision of the surgeon. Of course, the surgeon will have specified the lens properties appropriate to the ultimate axial location at which he intends to make his implant. In all cases, finish-ground optical quality glass is preferred at lenses 10, generally of 5 mm diameter and 0.3 mm thickness, although if tolerated by the body performed plastic lenses may be used.

Reference has been made to thin-sheet compliant flexible material for the described mounting structure. This represents my preference, and I indicate my further preference to employ a stable, strong, flexible polyimide, selected for commercial availability and autoclavability. The precise formation of described blank configurations is preferably achieved through photolithographic techniques which are described in one or more of the patent disclosures referred to in my said patent. With all forms except that of FIG. 16, the flexible sheet material is suitably 0.002-inch thick, but for the greater flexibility required of the FIG. 16 structure, a lesser thickness is desirable, in the range 0.0005 to 0.002 inch, preferably 0.001 inch.

The described structures will be seen to achieve all stated objects and to provide an improved product suited to particular needs, and especially adaptable to use of identical lithographically fabricated body blanks with different radii of iris-piloted support, as may be variously prescribed by the ophthalmological surgeon.

Throughout the specification, I have made reference to iris-stabilizing feet, at 22-23 and 29-30, for reasons of consistency with language in my said prior patents and disclosures. However, I note for the record that the word "haptic" is becoming more current in application to my extremely light-weight mounting structures, undoubtedly because of the extremely gentle compliant nature of their stabilizing engagement with the iris. This gentle action is particularly true for inward legs of foot structures 22-23 of the present case, wherein the extreme ends are cantilevered from the body structure 13 approximately twice the overall distance by which feet 29-30 extend from the body 13'. This fact, coupled with the substantially reduced radius at which the haptics 22-23 traverse the iris opening, is expected to materially reduce the likelihood of trauma attributable to the implanted device per se. In other radially compliant suspensions, as of the FIG. 16 variety, the ability to mount the lens independent of relying upon the iris for stabilization is also expected to materially reduce the likelihood of trauma due to implantation.

While the invention has been described in detail for the preferred forms shown, it will be understood that modifications may be made without departing from the claimed invention.

What is claimed is:

1. As an article of manufacture, an optically finished intraocular lens element having a generally circular periphery about its optical axis, and a mounting adapter for said lens element, said adapter comprising two circumferentially continuous annular body members each having a circular inner edge of diameter less than the diameter of said lens element, said body members being adjacent opposite axial sides of the peripheral region of said lens element and being connected to each other within a geometrical annulus radially outside said lens element, and a plurality of angularly spaced lens-positioning feet formed integrally with the inner edge of one of said body members, said feet extending radially outwardly of the periphery of said lens element and at axial offset from said lens element.

2. The article of claim 1, in which plural further lens-positioning feet are formed integrally with the outer edge of one of said body members and extend radially outwardly at angularly spaced locations which generally register with the locations of said first-mentioned plurality.

3. The article of claim 2, in which said plural further lens-positioning feet are integrally formed with said other body member.

4. The article of claim 1, in which plural further lens-positioning members formed integrally with the outer edge of one of said body members extend radially outward of the periphery of said lens element at angularly spaced locations, the radially outer extent of said further lens-positioning members being intermediate the range limits of pupil dilation, and the radially outward extent of said feet being such as to enter and engage the inner wall of a crystalline-lens sac following invasive surgery to remove cataracted material from the sac, whereby the surgery may be completed after placing said further lens-positioning members against the anterior wall of the iris and with said feet engaging the inner wall of the sac, and whereby after a period of sac regrowth into attachment to said feet, the pupil may be dilated to escape its lens-positioning engagement, thereby releasing the lens and the remainder of its mounting adapter for repositioning on the posterior side of the iris.

5. The article of claim 1, in which at least one angularly localized further lens-positioning member formed integrally with the outer edge of one of said body members extends radially outward of the periphery of said lens element, said further lens-positioning member having an opening for suture reception at a radius exceeding the maximum dilation radius of an iris opening.

6. The article of claim 1, in which at least one angularly localized further lens-positioning member formed integrally with the outer edge of one of said body members extends radially outward of the periphery of said lens element, said further lens-positioning member including angularly divergent bifurcated formations at a radius exceeding the maximum dilation radius of an iris opening.

7. As an article of manufacture, an optically finished intraocular lens element having a generally circular periphery about its optical axis, and a mounting adapter for said lens element, said adapter comprising two circumferentially continuous annular body members having a circular inner edge of diameter less than the diameter of said lens element, said body members being adjacent opposite axial sides of the peripheral region of said lens element and being connected to each other within a geometrical annulus radially outside said lens element, and a plurality of angularly spaced lens-positioning feet extending radially outwardly of the periphery of said lens element and having radially compliant integral connection to one of said body members.

8. The article of claim 7, in which each of said feet is characterized by an angularly extending outer limb having at one end thereof a single integral radially inward cantilevered connection to said one body member.

9. The article of claim 8, wherein said one body member is of compliant sheet material and wherein the width of said outer limb is relatively narrow at juncture with said cantilevered connection, whereby said outer limb is adaptable to relatively localized compliant articulation at said juncture.

10. The article of claim 8, wherein said one body member is of compliant sheet material and wherein the width of said outer limb is relatively narrow at substantially its angular midpoint, whereby said outer limb is adaptable to relatively localized compliant articulation at said midpoint.

11. The article of claim 8, wherein said one body member is of compliant sheet material and wherein the width of said cantilevered connection is relatively narrow at a location radially inward of outer-limb juncture, whereby said outer limb is adaptable to variation in radially outer extent through relatively localized compliant articulation at said location.

12. The article of claim 7, in which said one body member is of compliant sheet material and each of said feet is characterized by an angularly extending limb having at angularly spaced locations separate integral radially inward compliant connections to said one body member.

13. The article of claim 12, in which the width of said outer limb is relatively narrow at substantially its midpoint between the spaced radial connections thereto, whereby said outer limb is adaptable to relatively localized compliant articulation at said midpoint.

14. The article of claim 8, in which the free end of said outer limb is characterized by an aperture for reception of a limb-manipulating control filament.

15. The article of claim 14, in which said one body member is of compliant sheet material and wherein the width of said cantilevered connection is relatively narrow at a location radially inward of outer-limb juncture, whereby filament manipulation via the apertures at the outer-limb ends is operative to transiently reduce the overall radial extent of said article for ease of surgical manipulation.

16. As an article of manufacture, an optically finished intraocular lens element having a generally circular periphery about its optical axis, and a mounting adapter for said lens element, said adapter comprising two circumferentially continuous annular body members each having a circular inner edge of diameter less than the diameter of said lens element, said body members being adjacent opposite axial sides of the peripheral region of said lens element and being connected to each other within a geometrical annulus radially outside said lens element, a radially undulating outer ring radially spaced from the locus of body-member engagement with the periphery of said lens element, and compliant generally radial limbs integrally connecting said ring with one of said body members.

17. The article of claim 16, in which said one body member is of compliant sheet material and in which said limbs are in generally diametrically opposed symmetry, whereby relatively extensive angular segments of said ring are defined in diametrically opposed relation and in angular interlace with the generally diametrically opposed regions of limb connection, whereby said segments are compliantly deflectable for ease of surgical manipulation.

18. The article of claim 17, in which each of said angular segments has a central aperture for reception of a segment-manipulating control filament.

19. The article of claim 1, wherein at least one of said feet comprises two legs integrally formed with said inner edge at angularly spaced locations along said inner edge, said legs being integrally connected at their remote ends.

20. The article of claim 19, wherein the number of said feet is two.

21. The article of claim 1, wherein each body member is of compliant sheet material, said feet being permanently bent from the sheet material of said one body member.

22. The article of claim 21, in which interlocking formations in the sheet material of both body members establish the connection of said body members at a plurality of angularly spaced locations.

23. The article of claim 22, in which for each body member said formations comprise corresponding slot formations within a first pair of diametrically opposed quadrants and corresponding hook formations within the remaining diametrically opposed pair of quadrants, the interconnection of said body members involving the hook formations of one body member engaged to the other body members via the slot formations of said other body member.

24. The article of claim 23, in which the hook formations of said other body member are engaged to said one body member via the slot formations of said one body member.

25. The article of claim 1, in which plural further lens-positioning feet formed integrally with the outer edge of one of said body members and extending radially outwardly at angularly spaced locations which are interlaced with the locations of said first-mentioned plurality.

26. The article of claim 25, in which said plural further lens-positioning feet are integrally formed with said other body member.

27. As an article of manufacture, an optically finished intraocular lens element having a generally circular periphery about its optical axis, and a mounting adapter for said lens element, said mounting adapter including a circumferentially continuous annular body having a circular inner edge of diameter less than the diameter of said lens element and being in circumferentially continuous radial overlap with at least one axial side of the peripheral region of said lens element, said adapter including means carried by said body member radially outside said lens element and in retaining engagement with the other axial side of the peripheral region of said lens element, and a plurality of angularly spaced lens-positioning feet formed integrally with the inner edge of said body, said feet extending radially outwardly of the periphery of said lens element and at axial offset from said lens element.

28. The article of claim 27, in which said annular body comprises a first annular member of compliant sheet material, and in which said means comprises a second annular member of compliant sheet material engaged to said first annular member.

29. The article of claim 27, in which said means comprises plural retaining-lug formations formed integrally with said body at angularly spaced locations.

30. The article of claim 29, in which said retaining-lug formations are circumferentially interconnected at the location of retaining engagement with said other axial side.

31. As an article of manufacture, a mounting-adapter element of compliant sheet material for iris-stabilized mounting of an intraocular lens element of circular peripheral contour, comprising a body member having a circumferentially continuous centrally open inner-rim formation of inner diameter less than the outer diameter of the lens element and for axial-retaining abutment with one axial side of the rim of the lens element, means carried at a radially outer region of said body member for axial-retaining abutment with the other axial side of the rim of the lens element, and a plurality of angularly spaced lens-positioning feet formed integrally with the inner edge of said body member, said feet extending radially outwardly of the rim diameter of the lens element and at axial offset from said body member in the direction away from said means.

32. The article of claim 31, in which said means comprises a second body member having a circumferentially continuous centrally open inner-rim formation of inner diameter less than the outer diameter of the lens element.

33. The article of claim 31, in which said means comprises plural retaining-lug formations formed integrally with said body at angularly spaced locations.

34. The article of claim 33, in which said retaining-lug formations have interengageable formations for establishing their circumferential interconnection at the location for lens-retaining abutment with said other axial side.

35. The article of claim 31, in which said axial offset is substantially half a millimeter.

36. The article of claim 1, in which plural further lens-positioning members formed integrally with the outer edge of one of said body members extend radially outwardly of the periphery of said lens element at angularly spaced locations.

37. The article of claim 36, in which at least one of said further lens-positioning members has a peripherally enclosed opening therein.

38. As an article of manufacture, an optically finished intraocular lens element having a generally circular periphery about its optical axis, and a mounting adapter for said lens element, said adapter comprising two circumferentially continuous annular body members having a circular inner edge of diameter less than the diameter of said lens element, said body members being adjacent opposite axial sides of the peripheral region of said lens element and being connected to each other within a geometrical annulus radially outside said lens element, and a plurality of angularly spaced lens-positioning feet extending radially outwardly of the periphery of said lens element and having integral connection to one of said body members, said other body member having no foot projections and serving to define with said one body member an effectively circumferentially continuous base for tissue-growth attachment thereto.

39. The article of claim 38, in which said optical element is of glass and said body members are each of polyimide sheet material.

* * * * *